US012150837B2

(12) United States Patent
Farzin

(10) Patent No.: US 12,150,837 B2
(45) Date of Patent: Nov. 26, 2024

(54) DEVICE FOR EXTRACTING NASAL MUCUS OR EARWAX

(71) Applicant: Nina D. Farzin, Potomac, MD (US)

(72) Inventor: Nina D. Farzin, Potomac, MD (US)

( * ) Notice: Subject to any disclaimer, the term of this patent is extended or adjusted under 35 U.S.C. 154(b) by 40 days.

(21) Appl. No.: 17/412,185

(22) Filed: Aug. 25, 2021

(65) Prior Publication Data
US 2022/0062055 A1   Mar. 3, 2022

Related U.S. Application Data

(60) Provisional application No. 63/070,786, filed on Aug. 26, 2020.

(51) Int. Cl.
A61B 17/24 (2006.01)
A61B 90/00 (2016.01)
A61F 11/00 (2022.01)

(52) U.S. Cl.
CPC ............ *A61F 11/006* (2013.01); *A61B 17/24* (2013.01); *A61B 90/03* (2016.02); *A61B 90/36* (2016.02); *A61B 2017/242* (2013.01); *A61B 17/244* (2013.01); *A61B 2017/246* (2013.01); *A61B 2017/248* (2013.01); *A61B 2090/036* (2016.02)

(58) Field of Classification Search
CPC . A61F 11/006; A61B 17/24; A61B 2017/246; A61B 90/03; A61B 2090/036; A61B 2017/242; A61B 17/244; A61B 2017/248
USPC .......................................................... 606/162
See application file for complete search history.

(56) References Cited

U.S. PATENT DOCUMENTS

| 2,096,162 A | 10/1937 | Daley |
| D274,753 S | 7/1984 | Armstrong |
| D277,880 S | 3/1985 | Paczko |

(Continued)

FOREIGN PATENT DOCUMENTS

| CN | 202060971 U | 12/2011 |
| CN | 105748196 A | 7/2016 |

(Continued)

OTHER PUBLICATIONS

First office action on the merits (Non-Final Rejection) in U.S. Appl. No. 29/453,288, dated Aug. 14, 2015.

(Continued)

*Primary Examiner* — Shaun L David
*Assistant Examiner* — Mitchell Brian Hoag
(74) *Attorney, Agent, or Firm* — The Law Office of Patrick F. O'Reilly III, LLC

(57) ABSTRACT

A device for removing mucus from a nostril or earwax from an ear canal is disclosed herein. The device includes a light assembly, the light assembly including a light emitting device, the light emitting device configured to emit light so as to illuminate at least a portion of a nostril or an ear canal; and an extraction portion configured to be coupled to the light assembly, the extraction portion including an extraction element and a stop located adjacent to the extraction element, the extraction element sized and configured to fit within the nostril or the ear canal for extracting mucus or earwax, and the stop sized to prevent insertion of the stop into the nostril or the ear canal and limit the depth that the extraction element is able to be inserted into the nostril or the ear canal.

18 Claims, 14 Drawing Sheets

(56) References Cited

U.S. PATENT DOCUMENTS

| | | | |
|---|---|---|---|
| D335,927 S | | 5/1993 | Burgio et al. |
| 5,209,757 A | * | 5/1993 | Krug .................... A61F 11/006 606/162 |
| 5,219,350 A | * | 6/1993 | Emerson ............ A61F 9/00709 606/162 |
| 5,334,212 A | | 8/1994 | Karell |
| 5,649,942 A | | 7/1997 | Yeh |
| 5,715,850 A | | 2/1998 | Markgraaf |
| 5,888,199 A | * | 3/1999 | Karell .................... A61F 11/006 606/162 |
| D423,669 S | | 4/2000 | Huttner et al. |
| D439,338 S | | 3/2001 | Huttner et al. |
| D444,556 S | | 7/2001 | Estrem |
| D447,237 S | | 8/2001 | Huttner et al. |
| 6,270,510 B1 | | 8/2001 | Westendorf |
| 6,475,172 B1 | * | 11/2002 | Hall ....................... A61B 17/24 601/139 |
| D470,238 S | | 2/2003 | Boggs |
| D489,131 S | | 4/2004 | Gojcaj |
| D490,523 S | | 5/2004 | Samborski |
| 6,776,786 B2 | | 8/2004 | Kim |
| D525,365 S | | 7/2006 | Mills |
| D539,426 S | | 3/2007 | Callaghan |
| 7,306,558 B2 | * | 12/2007 | Peters ................. A61M 60/289 600/16 |
| D567,373 S | | 4/2008 | Irby |
| D583,045 S | | 12/2008 | Leal |
| D631,957 S | | 2/2011 | Perez et al. |
| D652,925 S | | 1/2012 | Nanda |
| 9,278,030 B2 | | 3/2016 | Olson |
| D771,814 S | | 11/2016 | Farzin |
| 9,480,605 B2 | | 11/2016 | Farzin |
| D847,993 S | | 5/2019 | Olson |
| 10,335,319 B2 | | 7/2019 | Wasicek et al. |
| D896,382 S | | 9/2020 | Fan |
| D926,981 S | | 8/2021 | Farzin |
| 2003/0187469 A1 | * | 10/2003 | Olson .................... A61F 11/006 606/162 |
| 2003/0229322 A1 | * | 12/2003 | Macrae ............... A61M 3/0279 604/514 |
| 2004/0249244 A1 | * | 12/2004 | Koda .................... A61F 11/006 600/200 |
| 2005/0080354 A1 | | 4/2005 | Crossley |
| 2005/0096678 A1 | | 5/2005 | Olson |
| 2006/0085018 A1 | | 4/2006 | Clevenger |
| 2007/0009368 A1 | * | 1/2007 | Yang ...................... A61M 1/79 417/312 |
| 2008/0142385 A1 | | 6/2008 | Stein et al. |
| 2008/0300527 A1 | | 12/2008 | Bivins |
| 2009/0300867 A1 | | 12/2009 | Farhoudi |
| 2010/0042122 A1 | * | 2/2010 | Shaw, Jr. ............ A61F 11/006 606/162 |
| 2011/0066172 A1 | | 3/2011 | Silverstein |
| 2012/0283616 A1 | | 11/2012 | Edme et al. |
| 2015/0018861 A1 | | 1/2015 | Olson |
| 2015/0039003 A1 | * | 2/2015 | Wilson .................... A61B 17/24 606/162 |
| 2015/0127036 A1 | * | 5/2015 | Farzin .................. A61F 11/006 606/162 |
| 2016/0310154 A1 | | 10/2016 | Harkless |
| 2017/0354541 A1 | * | 12/2017 | Olson .................... A61F 11/006 |
| 2019/0307322 A1 | * | 10/2019 | Wujciak ............. A61B 1/00101 |
| 2020/0214895 A1 | * | 7/2020 | Olson .................... A61F 11/006 |
| 2021/0038434 A1 | * | 2/2021 | Giaquinto ............. A61F 11/006 |

FOREIGN PATENT DOCUMENTS

| | | | | |
|---|---|---|---|---|
| CN | 106821593 A | | 6/2017 | |
| CN | 208243696 U | | 12/2018 | |
| CN | 111281659 A | | 6/2020 | |
| DE | 202017005711 U1 | | 2/2018 | |
| EM | 001211965-0001 | | 5/2010 | |
| EM | 002614396-0001 | | 1/2015 | |
| EM | 002614396-0002 | | 1/2015 | |
| EM | 002614396-0003 | | 1/2015 | |
| EM | 002614396-0005 | | 1/2015 | |
| EM | 002614396-0006 | | 1/2015 | |
| EP | 1138292 A1 | | 10/2001 | |
| IL | 61032 | | 10/2019 | |
| KR | 101320012 B1 | * | 10/2013 | ............. A61B 17/70 |
| KR | 20220001168 U | * | 5/2022 | ............. A61F 11/00 |
| SI | 9550140-0001 | | 4/1996 | |
| WO | WO-9733530 A2 | * | 9/1997 | ............. A61B 1/227 |
| WO | 2010140144 A1 | | 12/2010 | |

OTHER PUBLICATIONS

Oogiebear—The Safe Nasal Booger and Ear Cleaner—Baby Shower Registry Essential, https://www.pinterest.com.au/pin/721701909014261327/.

Bebon Angel—The Better Nose Cleaner and Ear Cleaner for Babies Visibly More Effective Than Nasal Aspirator https://www.amazon.de/-/en/Bebon-Angel-Cleaner-Effective-Aspirator/dp/B07H3SD3P8.

International Search Report Form, PCT/ISA/220, Application No. PCT/US2014/063363, date of mailing: Jan. 30, 2015, 14 pages.

First office action on the merits (Non-Final Rejection) in U.S. Appl. No. 14/072,123, dated Aug. 11, 2015.

Second office action on the merits (Non-Final Rejection) in U.S. Appl. No. 14/072,123, dated Feb. 9, 2016.

International Search Report Form PCT/ISA/220, Application No. PCT/US2021/047709, date of mailing: Dec. 8, 2021, 2 pages.

Written Opinion of the International Searching Authority, PCT Form 237, Application No. PCT/US2021/047709, date of mailing: Dec. 8, 2021, 9 pages.

* cited by examiner

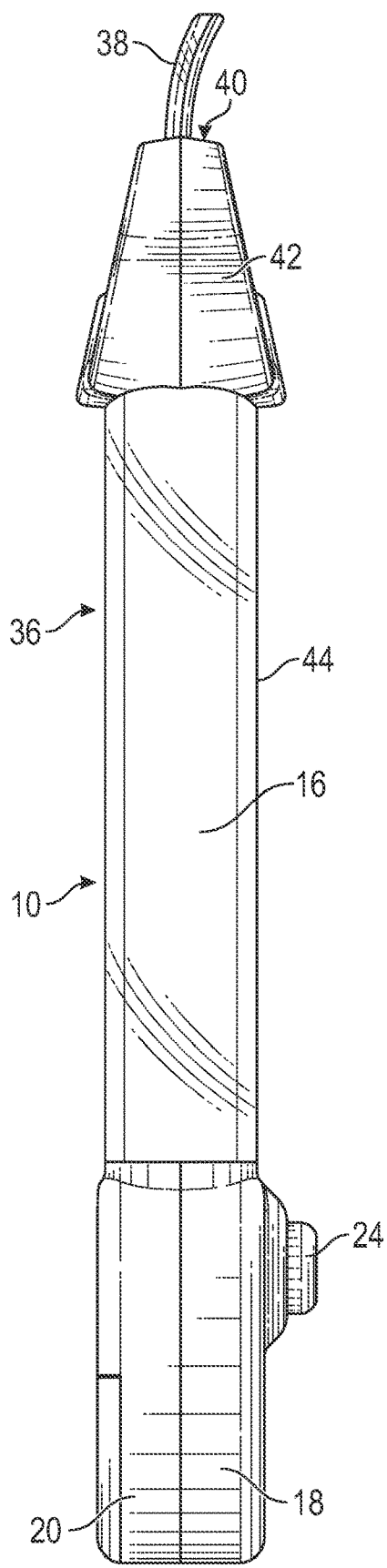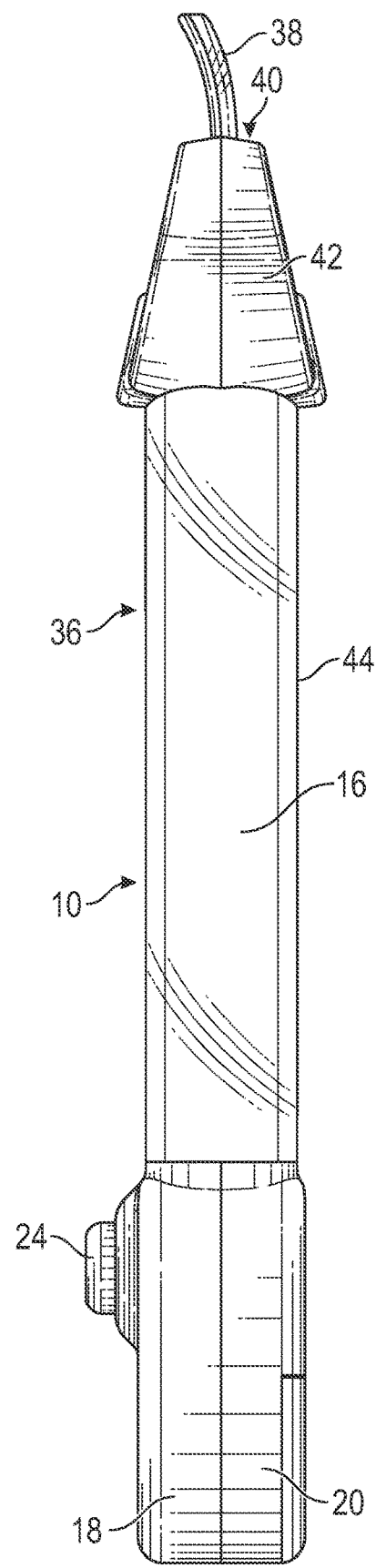
FIG. 4
FIG. 5

DEVICE FOR EXTRACTING NASAL MUCUS OR EARWAX

CROSS-REFERENCE TO RELATED APPLICATIONS

This patent application claims priority to, and incorporates by reference in its entirety, U.S. Provisional Patent Application No. 63/070,786, entitled "Device For Extracting Nasal Mucus Or Earwax", filed on Aug. 26, 2020.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF DISCLOSURE

1. Field of the Disclosure

This disclosure relates to a device for removing a material from a nostril or ear canal. More particularly, the disclosure relates to a device that includes a light to illuminate a nostril or ear canal while the device is being used to remove material from the nostril or ear canal.

2. Background

The accumulation of dried nasal mucus in the nostrils can make breathing difficult. Additionally, it is believed by many that excess mucus and debris should be removed from the nostrils and sinus passages to promote health and relieve or decrease symptoms associated with rhinitis or sinusitis, including facial pain, headache, halitosis, cough, anterior rhinorrhea and nasal congestion.

A known technique for cleansing or removing excess mucus and debris from the nostrils is nasal irrigation (also known as nasal lavage or nasal douche), which is a personal hygiene practice involving flushing the nasal cavity with water or a saline solution, and encompasses pouring the solution from a container into one nostril and allowing it to run out the other nostril and into a sink or spraying the solution into the nostrils. Nasal irrigation techniques can be difficult, uncomfortable and messy.

Other known techniques have generally involved removing mucus (wet or dry) from the nostrils with a finger or a cotton swab or similar device. Use of a finger to remove mucus (wet or dry) is often ineffective and is generally shunned as a disgusting practice. Use of devices such as cotton swabs can also be ineffective and could result in injury and/or extreme discomfort. The use of a finger, cotton swabs or other known devices for removing mucus can actually push the mucus up the nostril, increasing discomfort and/or exacerbating breathing difficulties. These devices and techniques are especially unsuitable for infants and children because of the smaller size (e.g., diameter) of their nostrils, which prevents fingers or other objects from being used to remove mucus. Further, it can be dangerous to insert fingers or other known devices into nostrils of subjects, especially infants and small children.

Expelling mucus by forcefully exhaling through the nostrils ("blowing one's nose") is generally ineffective at removing dried mucus material.

Nasal aspirators for evacuating mucus is somewhat effective for removing wet mucus from the nostrils, but is generally incapable of removing dried mucus, especially mucus encrusted on nasal tissue.

Like the removal of mucus from the nostrils, the removal of earwax from the ears also presents various challenges, particularly when the earwax is being removed from the small ears of infants and children. Also, it is often very difficult to see the mucus in the nostrils and the earwax in the ears during the removal process, particularly when the ambient light level is low (e.g., at night).

None of the aforementioned techniques or devices is well suited for removing dried mucus (also known as "boogers") from nostrils or for removing earwax from ear canals. The aforementioned techniques are particularly unsuitable for removing dried mucus from the nostrils of infants or earwax from the ear canals of infants. Also, none of the aforementioned techniques provide a means for illuminating the nostrils or ear canals when removing mucus from the nostrils or earwax from the ear canals.

SUMMARY OF THE DISCLOSURE

Accordingly, the present disclosure is directed to a device for extracting nasal mucus or earwax that substantially obviates one or more problems resulting from the limitations and deficiencies of the related art.

In accordance with one or more embodiments of the present disclosure, there is provided a device for removing mucus from a nostril or earwax from an ear canal. The device includes a light assembly, the light assembly including a light emitting device, the light emitting device configured to emit light so as to illuminate at least a portion of a nostril or an ear canal; and an extraction portion configured to be coupled to the light assembly, the extraction portion including an extraction element and a stop located adjacent to the extraction element, the extraction element sized and configured to fit within the nostril or the ear canal for extracting mucus or earwax, and the stop sized to prevent insertion of the stop into the nostril or the ear canal and limit the depth that the extraction element is able to be inserted into the nostril or the ear canal.

In a further embodiment of the present disclosure, the extraction element of the extraction portion is in a form of a bowl, the bowl including a sidewall and a bottom wall connected to the sidewall.

In yet a further embodiment, the bottom wall of the bowl is generally flat.

In still a further embodiment, the bowl has a length and a width, the length of the bowl being from about 100% to about 300% of the width of the bowl.

In yet a further embodiment, the stop has a width that is at least 200% of the width of the bowl.

In still a further embodiment, the extraction element of the extraction portion is in a form of a loop, the loop defining a loop opening.

In yet a further embodiment, the loop has a length and a width, the length of the loop being from about 100% to about 300% of the width of the loop.

In still a further embodiment, the stop has a width that is at least 200% of the width of the loop.

In yet a further embodiment, the extraction element of the extraction portion is formed from a material that is at least semi-translucent so that the light emitted by the light emitting device is able to be transmitted through the extraction element.

In still a further embodiment, the extraction portion is in a form of an extraction attachment that is configured to be removably coupled to the light assembly so that extraction attachments having different extraction elements are able to be interchangeably used with the light assembly.

In yet a further embodiment, the extraction attachment comprises an animal head portion forming the stop and a sleeve extending from the animal head portion, the sleeve configured to be removably coupled to a shaft portion of the light assembly.

In still a further embodiment, the light assembly further comprises a power source operatively coupled to the light emitting device, the power source configured to power the light emitting device, and the power source disposed inside a housing of the light assembly.

In yet a further embodiment, the light assembly further comprises a power switch operatively coupling the power source to the light emitting device, the power switch configured to activate and deactivate the light emitting device.

In still a further embodiment, the light emitting device is in a form of a light-emitting diode.

In accordance with one or more other embodiments of the present disclosure, there is provided a device for removing mucus from a nostril or earwax from an ear canal. The device includes a light assembly, the light assembly including a light emitting device, the light emitting device configured to emit light so as to illuminate at least a portion of a nostril or an ear canal; a first extraction portion configured to be coupled to the light assembly, the first extraction portion including a first extraction element and a first stop located adjacent to the first extraction element, the first extraction element sized and configured to fit within the nostril or the ear canal for extracting mucus or earwax, and the first stop sized to prevent insertion of the first stop into the nostril or the ear canal and limit the depth that the first extraction element is able to be inserted into the nostril or the ear canal; and a second extraction portion configured to be coupled to the light assembly, the second extraction portion including a second extraction element and a second stop located adjacent to the second extraction element, the second extraction element sized and configured to fit within the nostril or the ear canal for extracting mucus or earwax, and the second stop sized to prevent insertion of the second stop into the nostril or the ear canal and limit the depth that the second extraction element is able to be inserted into the nostril or the ear canal.

In a further embodiment of the present disclosure, the first extraction element of the first extraction portion is in a form of a bowl, the bowl including a sidewall and a bottom wall connected to the sidewall.

In yet a further embodiment, the second extraction element of the second extraction portion is in a form of a loop, the loop defining a loop opening.

In still a further embodiment, the first extraction portion is in a form of a first extraction attachment that is configured to be removably coupled to the light assembly, and the second extraction portion is in a form of a second extraction attachment that is configured to be removably coupled to the light assembly, the first extraction portion and the second extraction portion configured to be interchangeably used with the light assembly.

In yet a further embodiment, at least one of the first extraction attachment and the second extraction attachment comprises an animal head portion forming the first stop or the second stop and a sleeve extending from the animal head portion, the sleeve configured to be removably coupled to a shaft portion of the light assembly.

In still a further embodiment, at least one of the first extraction element and the second extraction element is formed from a material that is at least semi-translucent so that the light emitted by the light emitting device is able to be transmitted through the at least one of the first extraction element and the second extraction element.

It is to be understood that the foregoing general description and the following detailed description are merely exemplary and explanatory in nature. As such, the foregoing general description and the following detailed description should not be construed to limit the scope of the appended claims in any sense.

BRIEF DESCRIPTION OF THE SEVERAL VIEWS OF THE DRAWINGS

The device will now be described, by way of example, with reference to the accompanying drawings, in which:

FIG. 4 is a first side view of the device shown in FIG. 1;

FIG. 5 is an opposite second side view of the device shown in FIG. 1;

Throughout the figures, the same parts are always denoted using the same reference characters so that, as a general rule, they will only be described once.

DETAILED DESCRIPTION OF ILLUSTRATED EMBODIMENT(S)

Figure 1:
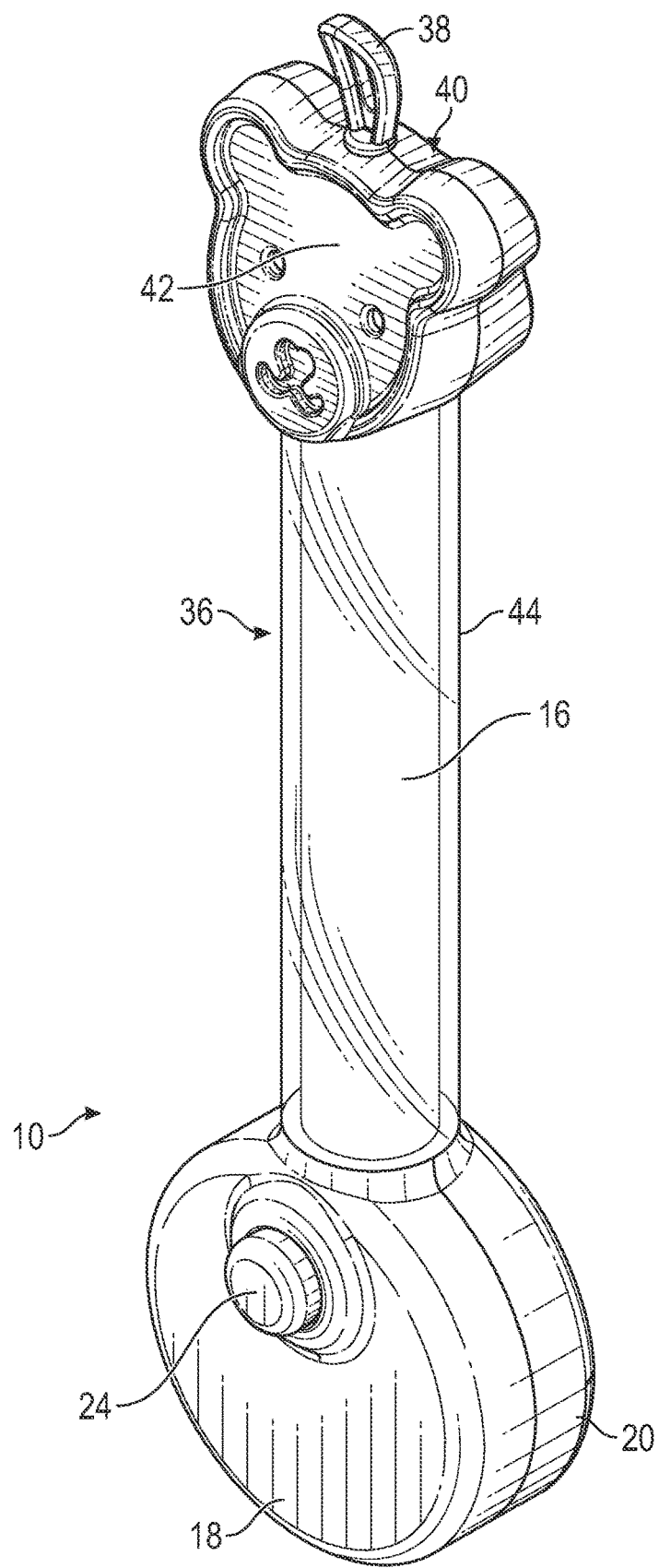
FIG. 1 is one perspective view of a device for removing mucus from a nostril or earwax from an ear canal, according to an illustrative embodiment of the disclosure, wherein a loop attachment is provided on the light assembly of the device.
Figure 2:
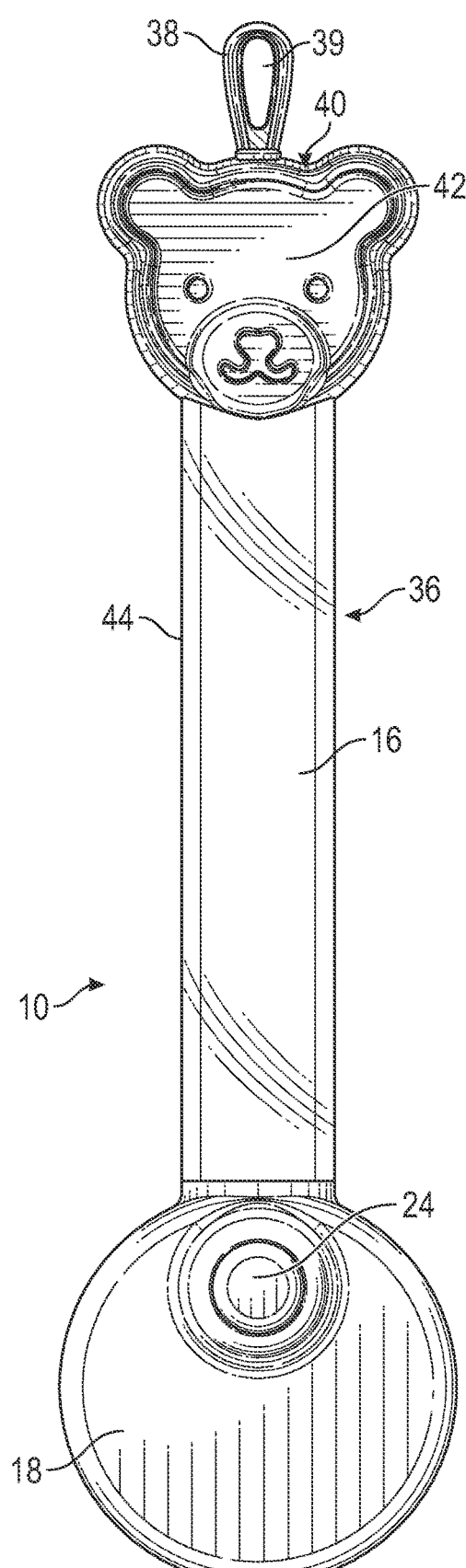
FIG. 2 is a front elevational view of the device shown in FIG. 1.
Figure 3:
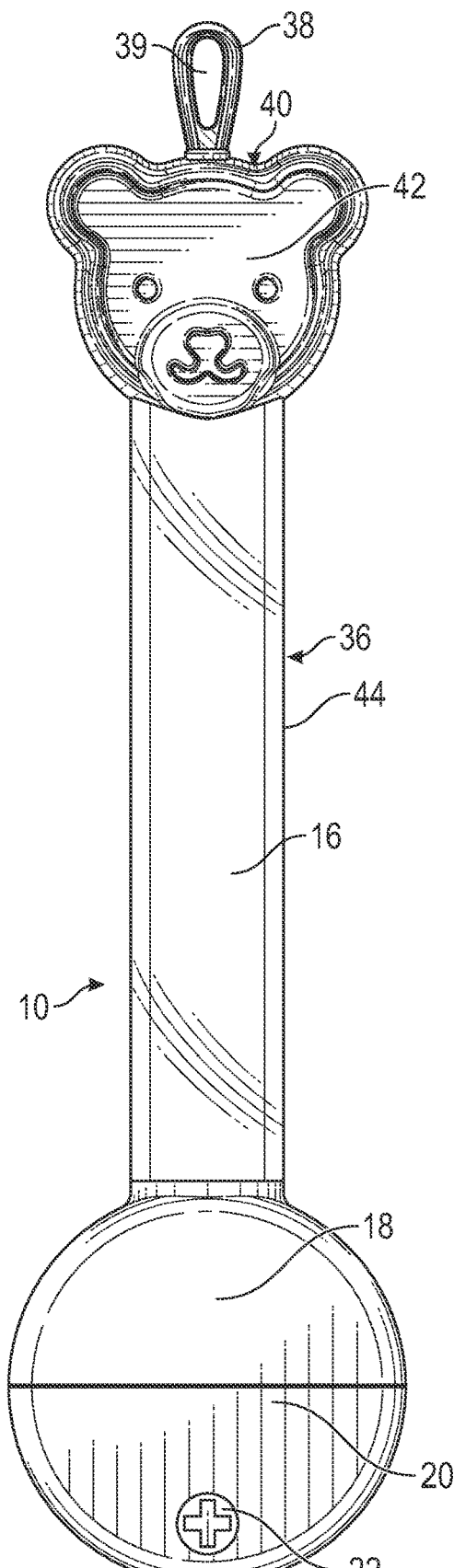
FIG. 3 is a rear elevational view of the device shown in FIG. 1.
Figure 6:
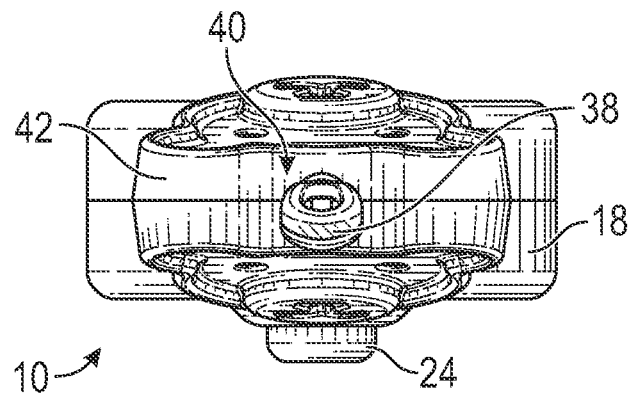
FIG. 6 is a first end view of the device shown in FIG. 1.
Figure 7:
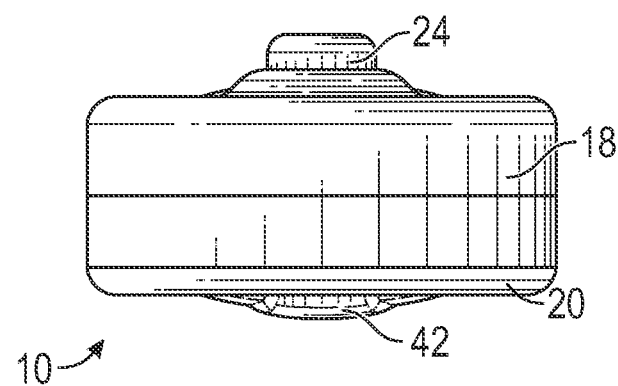
FIG. 7 is an opposite second end view of the device shown in FIG. 1.

An illustrative embodiment of a device for removing mucus from a nostril or earwax from an ear canal is seen generally at 10 in FIGS. 1-16. With initial reference to FIGS. 1, 8, 9, 16, and 17, it can be seen that the device 10 generally comprises a light assembly 12, the light assembly 12 including a light emitting device 60 (see FIG. 21), the light emitting device 60 configured to emit light so as to illuminate at least a portion of a nostril or an ear canal; a first interchangeable extraction portion 26 configured to be coupled to the light assembly 12, the first extraction portion 26 including a first extraction element 28 and a first stop 30 located adjacent to the first extraction element 28, the first extraction element 28 sized and configured to fit within the nostril or the ear canal for extracting mucus or earwax, and the first stop 30 sized to prevent insertion of the first stop 30 into the nostril or the ear canal and limit the depth that the first extraction element 28 is able to be inserted into the nostril or the ear canal; and a second interchangeable extraction portion 36 configured to be coupled to the light assembly 12, the second extraction portion 36 including a second extraction element 38 and a second stop 40 located adjacent to the second extraction element 38, the second extraction element 38 sized and configured to fit within the nostril or the ear canal for extracting mucus or earwax, and the second stop 40 sized to prevent insertion of the second stop 40 into the nostril or the ear canal and limit the depth that the second extraction element 38 is able to be inserted into the nostril or the ear canal. In the illustrative embodiment, it is to be understood that the first and second extraction elements 28, 38 refer to structural members for extracting mucus or earwax.

Figure 8:
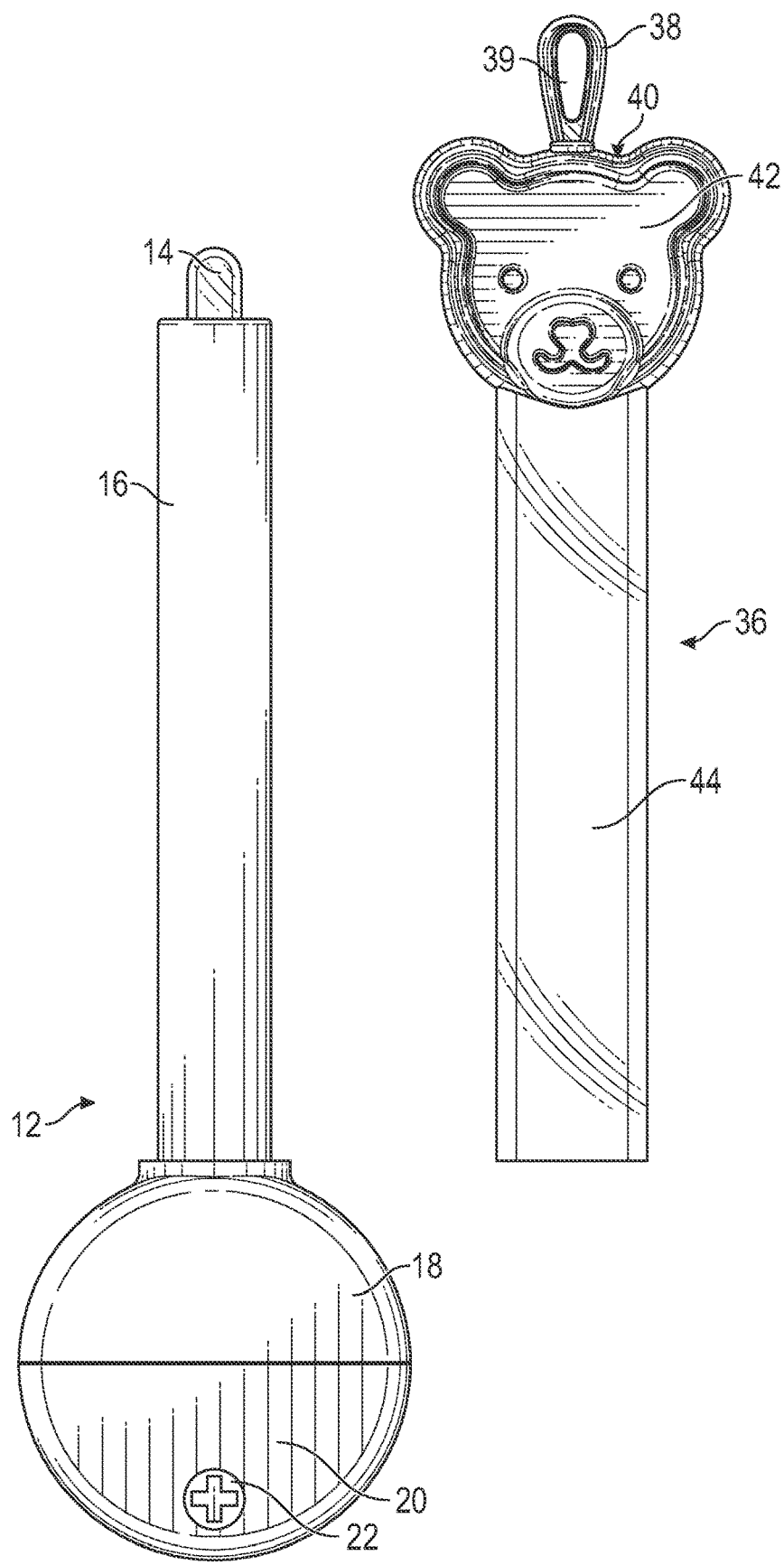
FIG. 8 is another rear elevational view of the device shown in FIG. 1, wherein the loop attachment is shown removed from the light assembly of the device.
Figure 16:
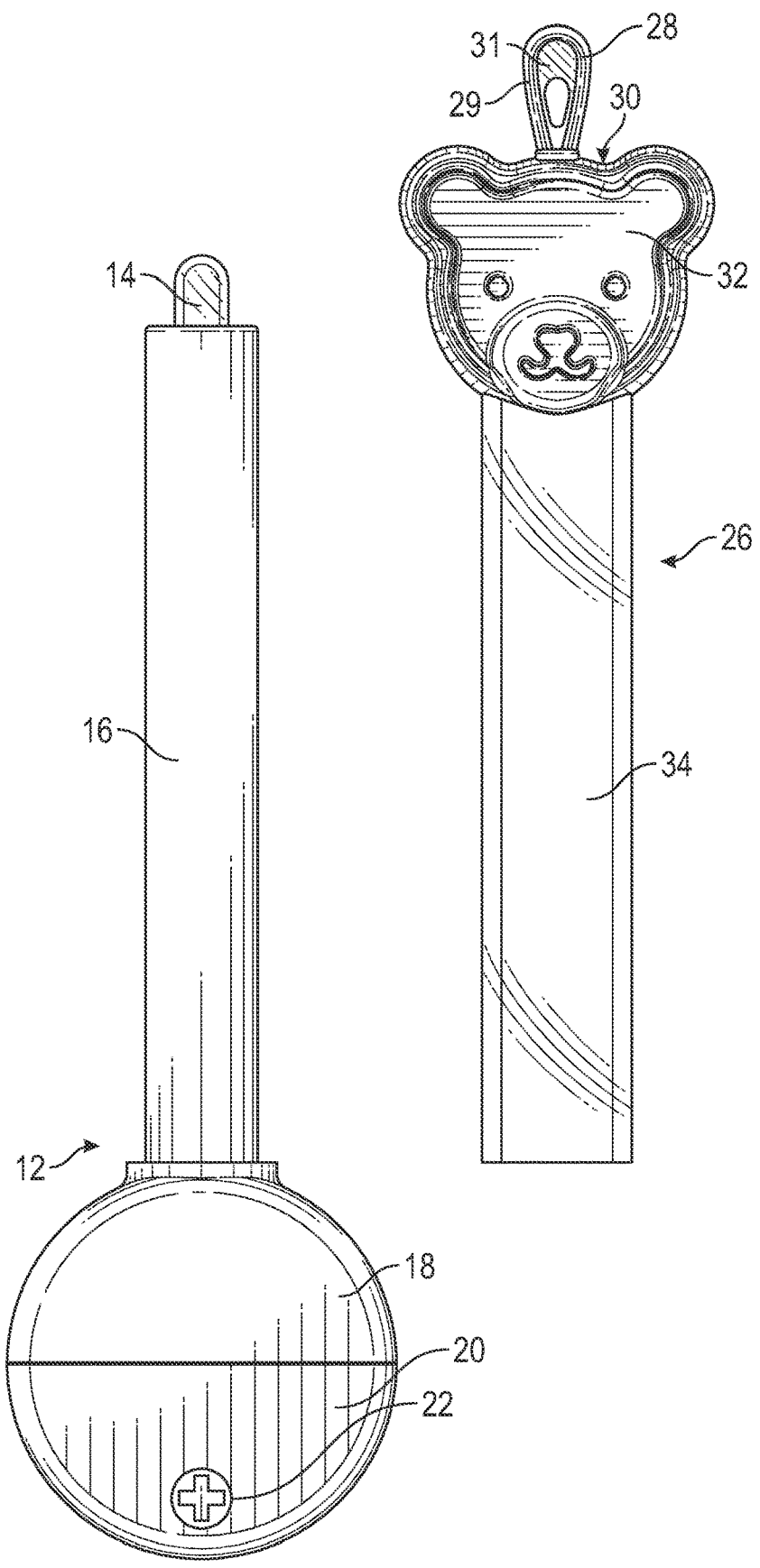
FIG. 16 is another rear elevational view of the device shown in FIG. 9, wherein the bowl attachment is shown removed from the light assembly of the device.

With combined reference to FIGS. 1, 8, 9, and 16, in the illustrative embodiment, the light assembly 12 generally comprises a shaft portion 16 that extends upwardly from a circular battery compartment end portion 18. The upper end of the shaft portion 16, which is opposite to the battery compartment end portion 18, comprises a dome-shaped light cover 14 that is disposed over the light emitting device 60. Also, as shown in the illustrative embodiment of FIGS. 1 and 9, it can be seen that the front side of the battery compartment end portion 18 comprises a light power button 24 for activating and deactivating the light emitting device 60 (see FIG. 21). The rear side of the battery compartment end portion 18 comprises a removable cover 20 for gaining access to the power source of the light assembly 12 (i.e., one or more batteries 52 that provide power for the light emitting device 60—see FIG. 21). In the illustrative embodiment, as shown in FIGS. 8 and 16, the removable cover 20 is removably secured to the housing of the battery compartment end portion 18 by a fastener 22 (e.g., screw 22). More specifically, in the illustrative embodiment, the battery compartment cover 20 is removably attached to the housing 62 by two projections 23 and the screw 22, which passes through the fastener aperture 21 in the cover 20 and is threadingly received within the fastener boss 70 of the housing section 64.

In the illustrative embodiment, the shaft portion 16 and the battery compartment end portion 18 forms a handle portion or grip portion of the device 10 that facilitates manipulation of the device 10 with either the first extraction portion 26 or the second extraction portion 36 attached to the light assembly 12.

The shaft portion 16 of the light assembly 12 is an elongate member having a generally circular cross-section that is of length, width and thickness that comfortably facilitates gripping of the device 10 during use. The length of shaft portion 16 can be from about 3 centimeters (cm) to about 10 cm, although a handle portion shorter than 3 cm or longer than 10 cm would also be expected to perform adequately. The length of the shaft portion 16 (the distance from the proximal end of the shaft portion 16 where it meets the battery compartment end portion 18 to the dome-shaped light cover 14 at the opposite or distal end of the shaft portion 16, or the distance between proximal and distal ends of the device) is typically at least 200% of the length of the extraction element 28 (i.e., the length of bowl 28).

In the illustrative embodiment, the first extraction portion is in a form of a first extraction attachment 26 that is removably coupled to the light assembly 12 (see FIG. 16), and the second extraction portion is in a form of a second extraction attachment 36 that is removably coupled to the light assembly 12 (see FIG. 8). The first extraction portion 26 and the second extraction portion 36 are configured to be interchangeably used with the light assembly 12 (i.e., a user can selectively attach either the first extraction portion 26 or the second extraction portion 36 to the light assembly 12 depending on the extraction element 28, 38 that is desired).

Figure 9:
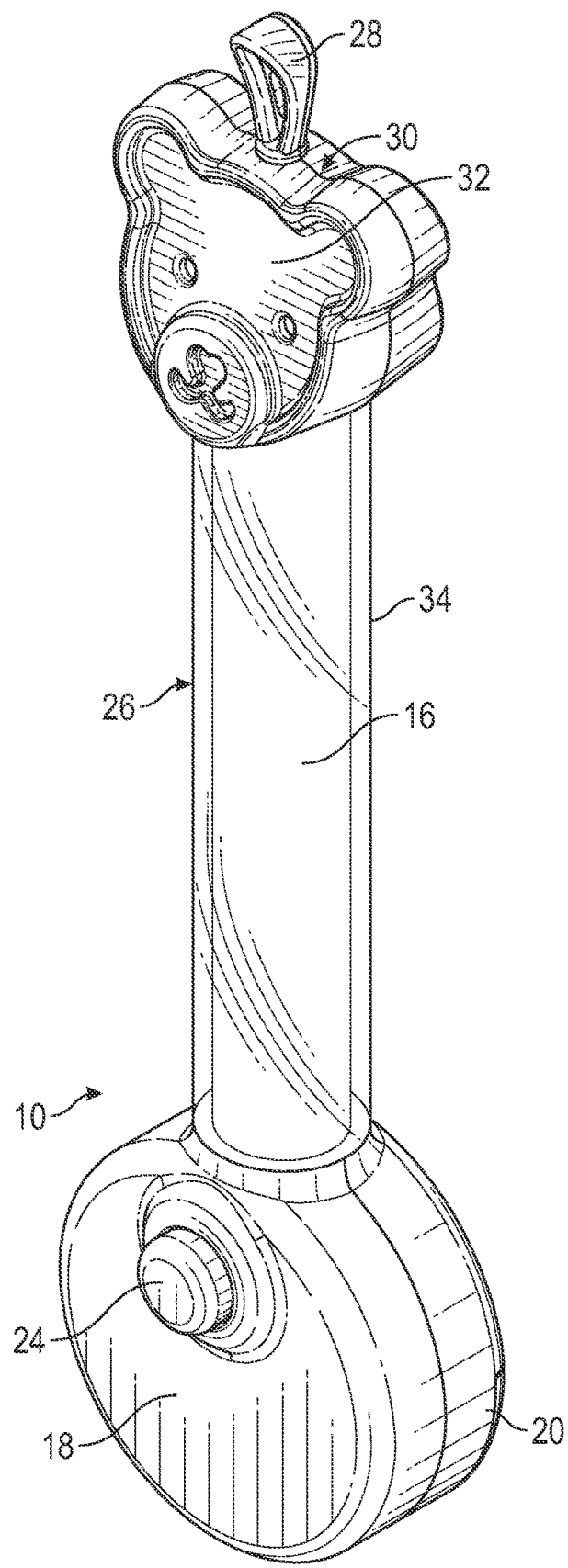
FIG. 9 is another perspective view of the device shown in FIG. 1, wherein a bowl attachment is provided on the light assembly of the device.

Referring again to FIGS. 9 and 16, in the illustrative embodiment, the first extraction attachment 26 comprises a head portion 32 forming the first stop 30 and a semi-transparent and translucent sleeve 34 extending downwardly from the head portion 32. As shown in FIG. 9, the sleeve 34 is configured to be removably coupled to the shaft portion 16 of the light assembly 12 (e.g., the sleeve 34 slips over and frictionally engages the shaft portion 16 of the light assembly 12). In the illustrative embodiment, the first extraction element 28 of the first extraction attachment 26 is in a form of a bowl 28. In FIG. 16, it can be seen that the bowl 28 includes sidewalls 29 and a bottom wall 31 connected to the sidewalls 29. The bottom wall of the bowl may be generally flat (i.e., the bottom wall may have a slight curvature due to typical molding irregularities, etc., but otherwise be flat). Bowl 28 is configured to allow earwax to be removed from an ear canal or allow mucus to be removed from a nostril using a scooping action. Bowl 28 is particularly useful for removing dried mucus from the nostrils or dried earwax from the ear canals (e.g., the bowl 28 is shaped so as to operate as a combined scraper and receptacle so as to grab and extract the dried mucus or earwax from the nostrils or ear canals).

Figure 10:
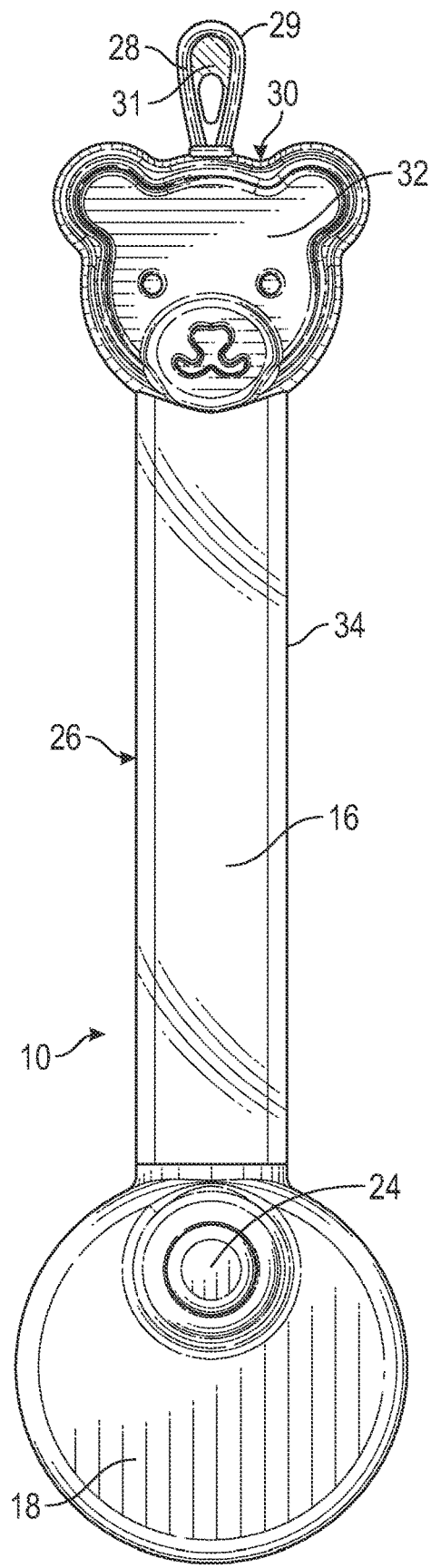
FIG. 10 is a front elevational view of the device shown in FIG. 9.
Figure 11:
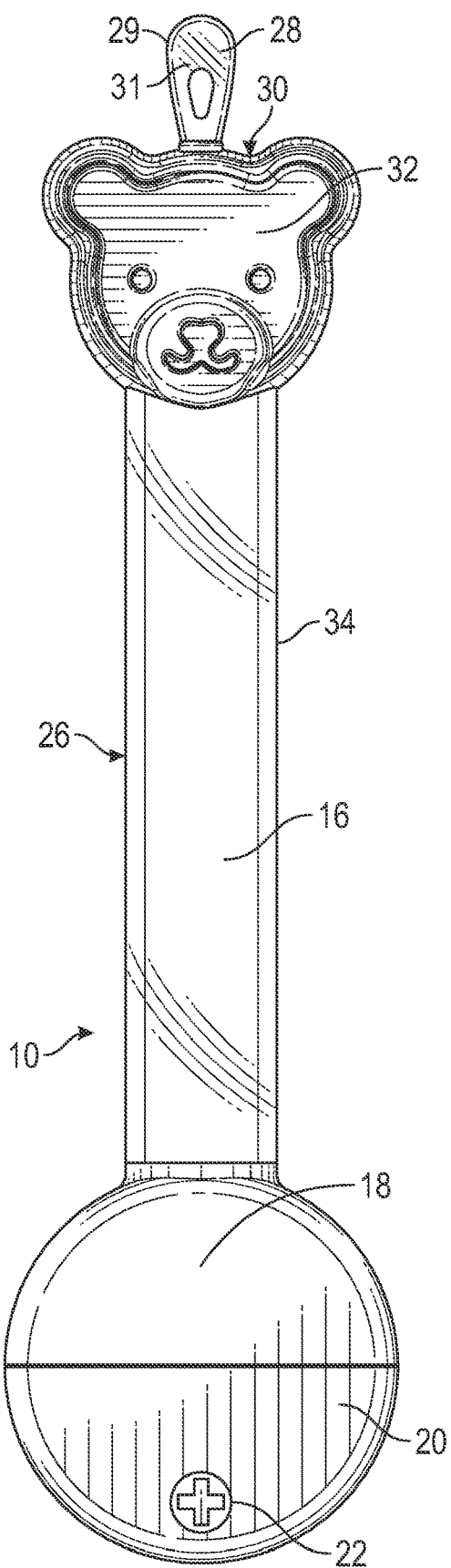
FIG. 11 is a rear elevational view of the device shown in FIG. 9.
Figure 12:
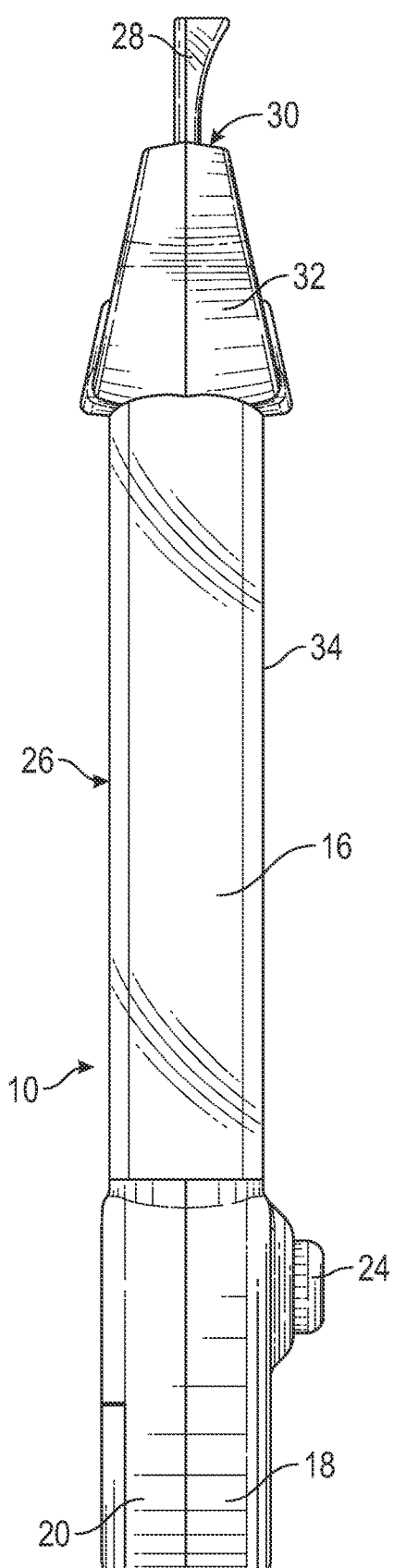
FIG. 12 is a first side view of the device shown in FIG. 9.
Figure 13:
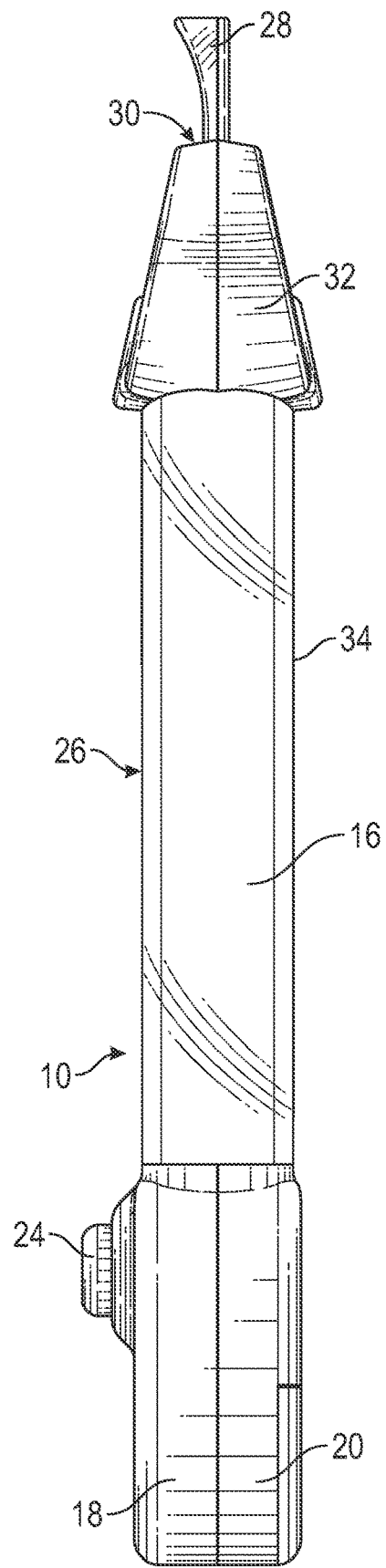
FIG. 13 is an opposite second side view of the device shown in FIG. 9.
Figure 14:
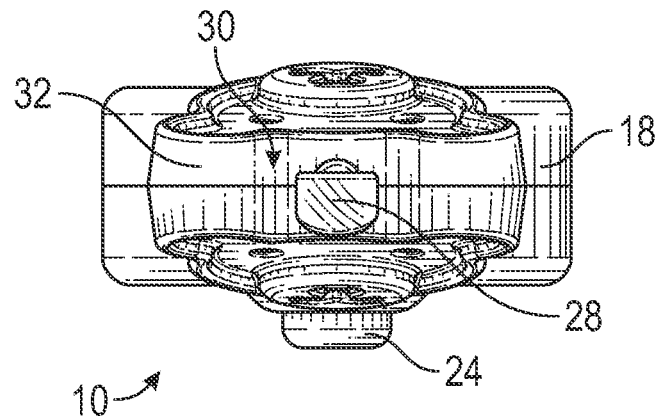
FIG. 14 is a first end view of the device shown in FIG. 9.
Figure 15:
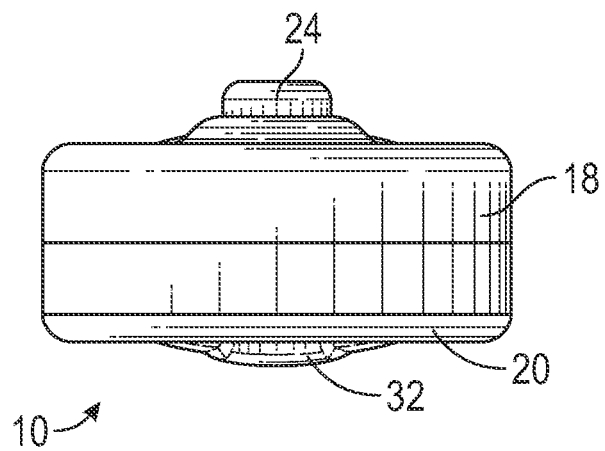
FIG. 15 is an opposite second end view of the device shown in FIG. 9.

In the illustrative embodiment, as shown in FIG. 10, the first stop 30 has a width perpendicular to the length of the semi-transparent and translucent sleeve 34 and the direction of insertion of bowl 28 into an ear canal or nostril that prevents insertion of stop 30 into the nostril or ear canal into which bowl 28 is inserted and limits the depth that bowl 28 can be inserted into the nostril or ear canal.

A suitable length of the bowl 28, measured from stop 30 to the distal end of bowl 28 is from about 5 mm to about 10 mm. This is a length that can effectively reach most mucus in the nostril or earwax in an ear canal, while preventing injury or extreme discomfort through overly deep penetration into the nostrils or ear canals. Typically, the width of bowl 28 is less than the length, with a suitable width (the largest dimension perpendicular to the length direction) of bowl 28 being from about 3 mm to about 10 mm. The length of bowl 28 is typically from about 100% to 300% of the width of bowl 28 (i.e., from about equal to the width to about three times the width of the bowl). The depth of bowl 28 can be about equal to the width or less than the width of bowl 28 (e.g., about 2 mm to about 5 mm).

First stop 30 is sized and configured to prevent stop 30 from being inserted into the nostrils or ear canals. In the illustrative embodiment, stop 30 presents a broad relatively flat stop surface 30 (FIG. 14) that engages exterior portions of the nose or ear of a subject on which the device 10 is used to prevent over insertion of bowl 28 into the nostril or ear canal of the subject. The stop 30 may have a width that is at least 200% of the width of the bowl 28. For example, suitable dimensions for stop surface 30 are from about 12 mm to about 20 mm wide by from about 3 mm to about 10 mm in depth. Typically, stop surface 30 has a generally rectangular, flat surface, the illustrated embodiment deviating only slightly to accommodate the shape of the top of the decorative teddy-bear head design.

Referring again to FIGS. 1 and 8, in the illustrative embodiment, the second extraction attachment 36 comprises a head portion 42 forming the second stop 40 and a semi-transparent and translucent sleeve 44 extending downwardly from the head portion 42. As shown in FIG. 1, the sleeve 44 is configured to be removably coupled to the shaft portion 16 of the light assembly 12 (e.g., the sleeve 44 slips over and frictionally engages the shaft portion 16 of the light assembly 12). In the illustrative embodiment, the second extraction element 38 of the second extraction attachment 36 is in a form of a loop 38. In FIG. 8, it can be seen that the loop 38 defines a loop opening or loop hole 39. Loop 38 is configured to allow extraction of earwax from an ear canal or mucus from a nostril, and is particularly useful for removing gooey or wet mucus (i.e., mucus having sufficient moisture content to exhibit at least some fluid properties, such as the ability to flow when stressed) from the nostrils and wet earwax from the ear canals (e.g., the loop 38 is shaped so as to capture and extract the wet mucus or earwax from the nostrils or ear canals). While the loop 38 is in the form of a closed loop in the illustrative embodiment, it is to be understood that, in other embodiments, the loop may also be in the form of an open loop (i.e., where the loop wall does not extend a full 360 degrees).

In the illustrative embodiment, the length of loop 38 is typically from about 100% to 300% of the width of loop 38 (i.e., from about equal to the width to about three times the width of the loop). Loop 38 is capable of more easily extracting wet or slimy mucus or earwax than bowl 28, whereas bowl 28 is capable of more easily extracting dry mucus or earwax than loop 38. Thus, by providing two different types of extraction means (bowl 28 and loop 38), easier removal of a wider variety of mucus and earwax materials is facilitated.

In the illustrative embodiment, the dimensional characteristics (width, length and depth) of loop 38 and stop 40 are the same or substantially the same as those for bowl 28 and stop 30.

In the illustrative embodiment of the device 10, the head portion 32 and the head portion 42 are provided with ornamental features that resemble the head of a "teddy bear," with the top of the head forming stop surfaces 30, 40. However, various other ornamental features may be used. For example, in other embodiments, the head portions 32, 42 may take on other suitable shapes, such as but not limited to, the head shapes of other animals (e.g., other caricature animal head shapes). Alternatively, a flat stop surface without any ornamentation can be used.

Also, in other embodiments, the extraction element 28 and the stop 30 may be integrated into a single structure, and similarly, the extraction element 38 and the stop 40 may be integrated into a single structure (e.g., the extraction portions may be narrower at the tips thereof, and wider at the bases thereof to regulate the depth of insertion of the extraction portions).

With reference again to the perspective views of FIGS. 1 and 9, in the illustrative embodiment, the first extraction element (i.e., bowl 28) and the second extraction element (i.e., loop 38) are each formed from a material that is at least semi-translucent (e.g., a substantially clear polymeric material or plastic) so that the light emitted by the light emitting device 60 is able to be transmitted through the first extraction element 28 and the second extraction element 38 (i.e., the light shines through the first extraction element 28 and the second extraction element 38 at the distal end of the device 10). In other embodiments, the first extraction element 28 and the second extraction element 38 may be formed from other suitable translucent or semi-translucent materials.

Also, in the illustrative embodiment, the head portion 32 and the head portion 42 are each formed from a generally non-transparent material that is semi-translucent (i.e., some light emitted by the light emitting device 60 is able to be transmitted through the head portion 32 and the head portion 42, which may be formed from a lightly-colored material). Also, in the illustrative embodiment, the wall thickness of the head portion 32 and the head portion 42 is sufficiently thin so as to allow some light to pass therethrough. Advantageously, the partial translucent nature of the head portion 32 and the head portion 42 increases the illumination of the nostril or ear canal so that the earwax or mucus that is being extracted is more readily visible to a user of the device 10. In other embodiments, the head portion 32 and the head portion 42 may be formed from a material that is both transparent and translucent (e.g., a clear polymeric material or plastic).

In the illustrative embodiment, the device 10 described herein may be used to remove mucus from a nostril of an infant. Stop 30 or 40 prevents bowl 28 or loop 38 from accidently being inserted too deeply into the nostril of an infant. Also, the device 10 described herein may be used to remove earwax from an ear canal of an infant. Stop 30 or 40 prevents bowl 28 or loop 38 from accidently being inserted too deeply into the ear canal of the infant.

Now, with reference to the exploded view of FIG. 21, the electrical components of the illustrative device 10 will be explained in further detail. As shown in the illustrative embodiment of FIG. 21, the light assembly 12 further comprises a power source 52 operatively coupled to the light emitting device 60 by means of a positive electrical wire 56 and a negative electrical wire 58. Also, in the illustrative embodiment, the light assembly 12 further comprises a power switch 54 (i.e., an on/off switch 54) operatively coupling the power source 52 to the light emitting device 60 (see FIG. 21). The power switch 54 is configured to activate and deactivate the light emitting device 60 (i.e., turn the light 60 on or off) by regulating the current flow through the wire 58 when the light power button 24 is depressed by a user of the device 10. In the illustrative embodiment, the light emitting device 60 is in a form of a light-emitting diode (LED).

Turning again to FIG. 21, it can be seen that, in the illustrative embodiment, the power source of the device 10 may comprise a plurality of button cell batteries 52 (e.g., two (2) lithium button cell batteries) that are disposed in a battery recess formed within the housing 64 of the light assembly 12. For example, in the illustrative embodiment, the button cell or coin-cell batteries 52 may each comprise a lithium-type battery with an output voltage of approximately 3 volts (3V). In the illustrative embodiment, the button cell batteries 52 may provide up to 20 hours of battery life. Also, as shown in FIG. 21, the battery recess of the housing 64 may include a positive contact plate 46 and a negative contact plate 48 for electrically coupling the batteries 52 to the positive electrical wire 56 and the negative electrical wire 58, respectively. A spring 50 may be provided in the battery recess of the housing 64 so as to ensure that the batteries 52 remain in contact with the electrical contact plates 46, 48 (see FIG. 21).

Figure 21:
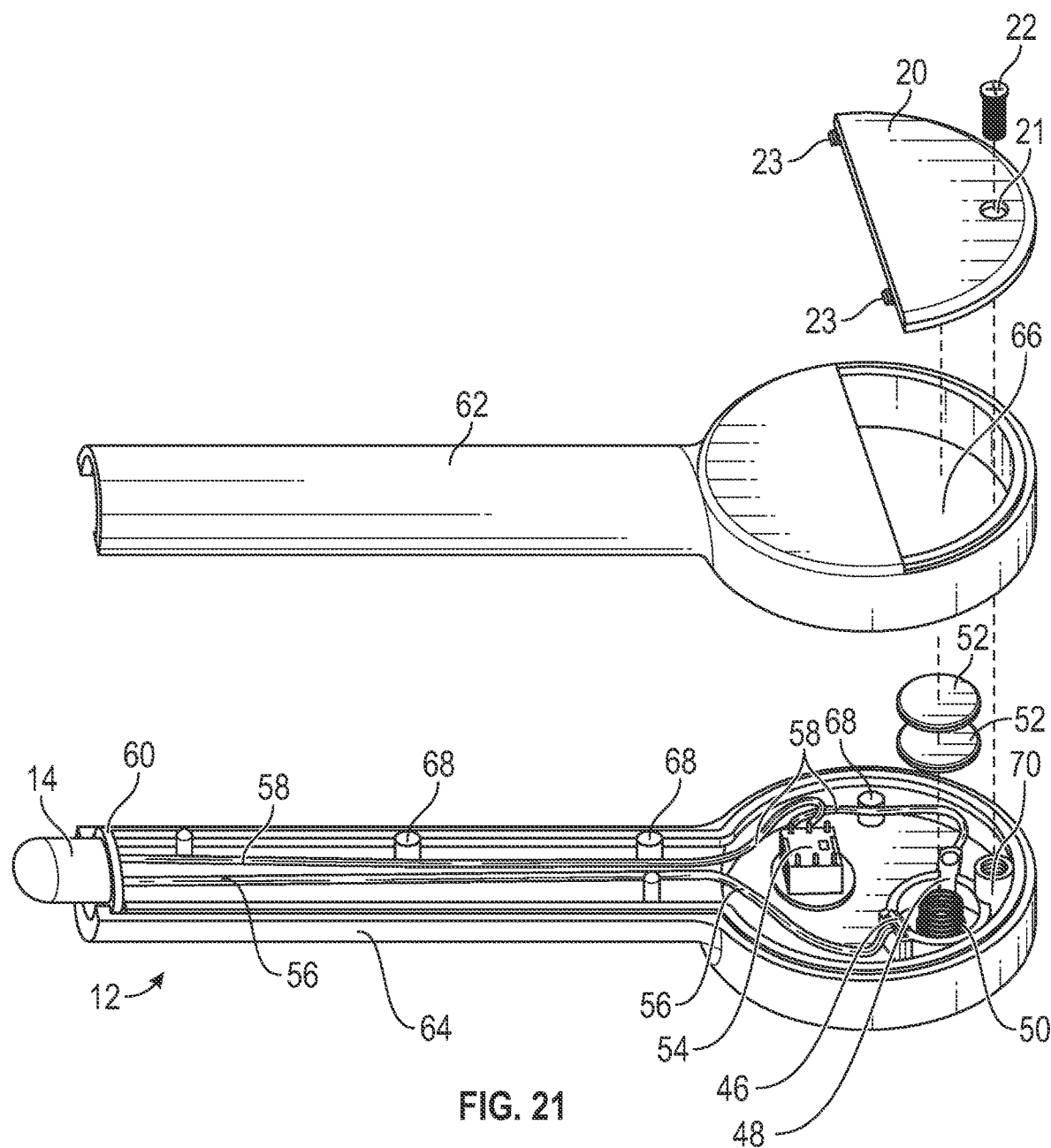
FIG. 21 is an exploded perspective view of the light assembly of the device shown in FIG. 1.

As shown in FIG. 21, in the illustrative embodiment, the housing of the light assembly 12 may comprise a clamshell-type housing with a first housing section 62 and a second housing section 64. In FIG. 21, it can be seen that the interior of the housing 64 may be provided with a plurality of housing standoffs 68 in order to enhance the structural rigidity of the housing, as well as to attach the housing sections 62, 64 to one another.

In the illustrative embodiment, when it is necessary to replace the batteries 52, a user removes the screw 22 from the battery compartment cover 20, which allows the cover 20 to be removed from the housing section 62, thereby enabling the user to access the batteries 52 through the battery compartment opening 66 of the housing section 62.

In other embodiments, other power sources may be used to provide power to the light 60 of the device 10. For example, a wired power source may be used (e.g., the device 10 may be connected to an electrical receptacle of a building). As another example, a wireless power source may be used (i.e., a wireless power source using inductive or capacitive technology).

Figure 17:
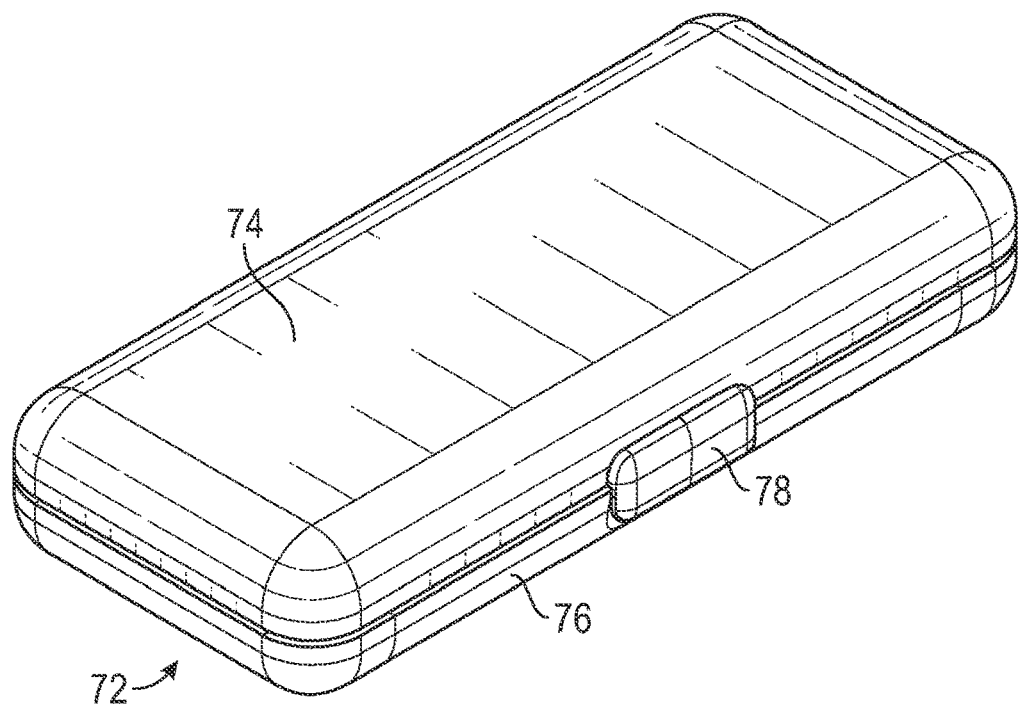
FIG. 17 is a perspective view of a carrying case for the device shown in FIG. 1, according to an illustrative embodiment of the disclosure, wherein the carrying case is depicted in a closed state.
Figure 18:
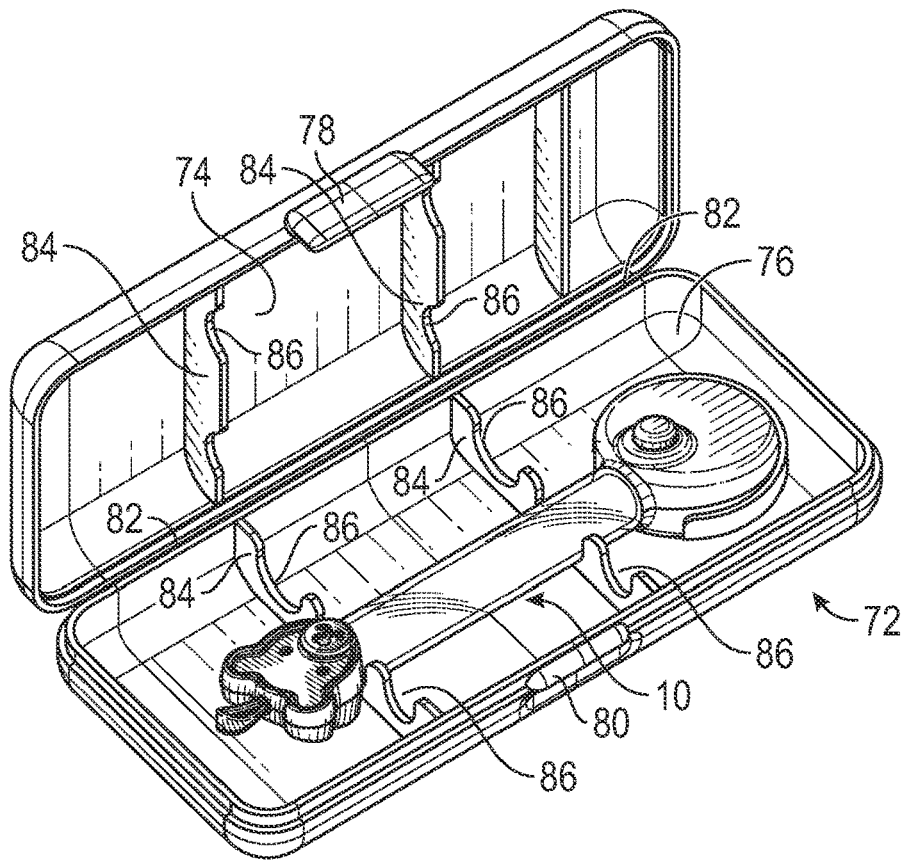
FIG. 18 is another perspective view of the carrying case shown in FIG. 17, wherein the carrying case is depicted in an open state.

Next, with reference to FIGS. 17 and 18, an illustrative embodiment of a carrying case 72 that may be used with the device 10 will be described. The carrying case 72 advantageously provides a convenient means by which the device 10 is able to be stored and transported in a hygienic manner. As shown in FIGS. 17 and 18, the carrying case 72 comprises an upper lid section 74 that is hingedly coupled to a lower base section 76 by a hinge portion 82. As such, by means of the hinge portion 82, the upper lid section 74 of the carrying case 72 is movable between the closed state of FIG. 17 and the open state of FIG. 18. Referring again to FIGS. 17 and 18, it can be seen that the carrying case 72 further comprises first and second latch portions 78, 80 for securing the upper lid section 74 in the closed position of FIG. 17. More specifically, in the illustrative embodiment, the upper lid section 74 comprises the first latch portion 78 and the lower base section 76 comprises the second latch portion 80. To maintain the upper lid section 74 in the closed position of FIG. 17, the first latch portion 78 snaps into place on the second latch portion 80. In addition, as shown in FIG. 18, the carrying case 72 further comprises a plurality of spaced-apart support rib members 84 with notches 86 formed therein for receiving the light assembly 12, the first extraction portion 26, and/or the second extraction portion 36 of the device 10. The spaced-apart support rib members 84 with notches 86 advantageously prevent the constituent components 12, 26, 36 of the device 10 from undesirably moving around inside the carrying case 72.

Figure 19:
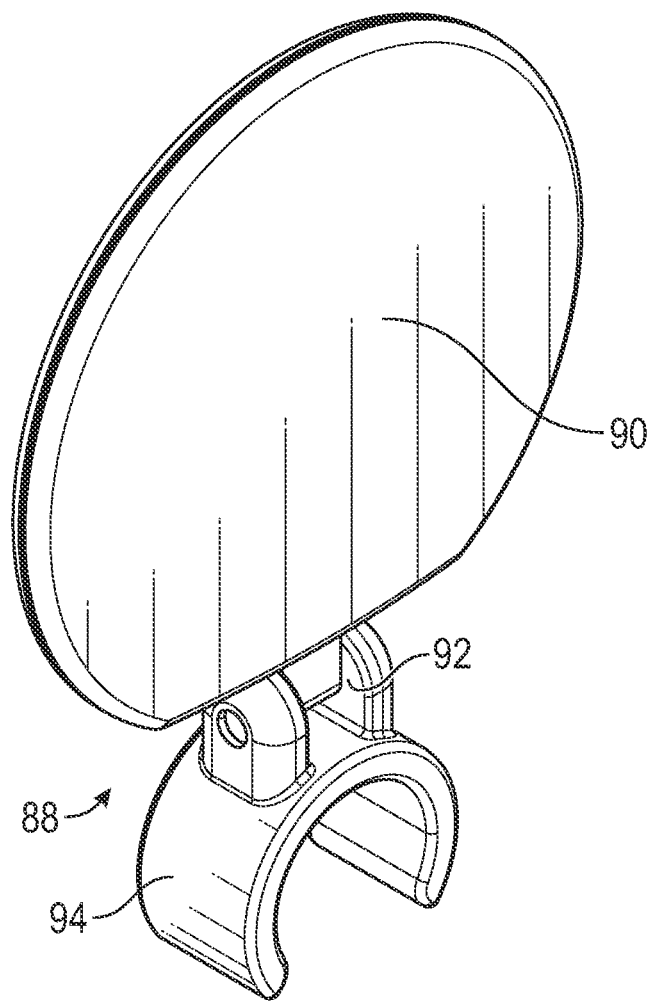
FIG. 19 is a perspective view of a magnifying glass accessory for the device shown in FIG. 1, according to an illustrative embodiment of the disclosure.
Figure 20:
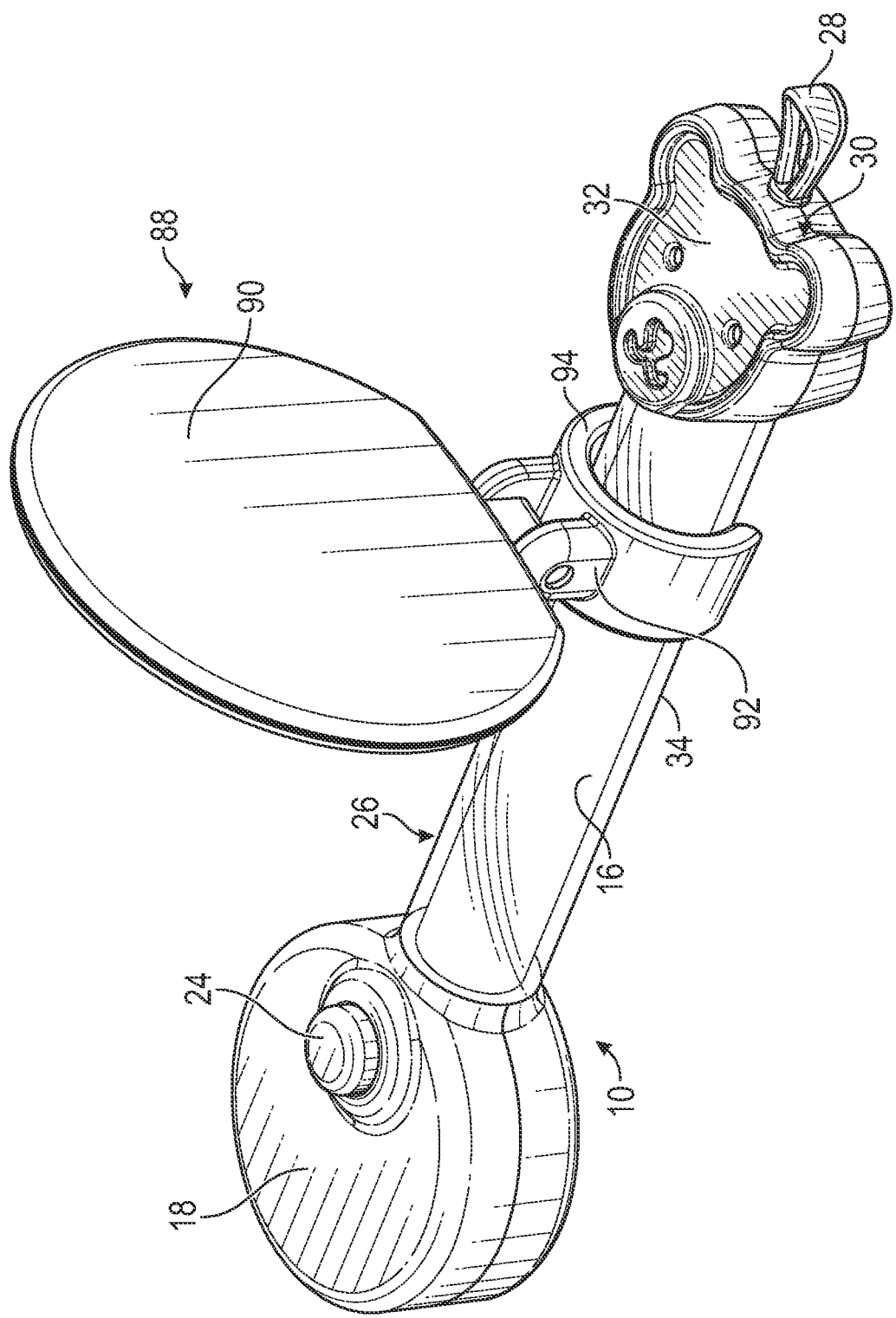
FIG. 20 is a perspective view depicting the magnifying glass accessory of FIG. 19 being disposed on the device shown in FIG. 9.

Now, with reference to FIGS. 19 and 20, an illustrative embodiment of a magnifying glass accessory 88 that may be used with the device 10 will be explained. When the magnifying glass accessory 88 is clipped onto the device 10 (e.g., as shown in FIG. 20), the magnifying glass accessory 88 can be used for visually enlarging portions of the nostrils or ear canals of the infant or other person on which the device 10 is being used. Initially, referring to FIG. 19, it can be seen that the magnifying glass accessory 88 generally comprises a magnifying disk portion 90, a hinge portion 92, and clip portion 94. In the illustrative embodiment, the magnifying disk portion 90 may comprise a convex lens that visually magnifies an object when a user looks at the object through the magnifying disk portion 90. The clip portion 94 of the magnifying glass accessory 88 may comprise a resilient clip that enables the magnifying glass accessory 88 to be removably clipped onto the sleeve portion 34, 44 of the extraction portion 26, 36 of the device 10 (e.g., as shown in FIG. 20). Also, as shown in the illustrative embodiment of FIGS. 19 and 20, the magnifying disk portion 90 is hingedly coupled to the clip portion 94 by means of the hinge portion 92 so that the magnifying disk portion 90 is able to rotate about the hinge axis so that different viewing angles of the user of the device 10 may be accommodated.

In one illustrative embodiment suitable for removing mucus from the nostrils of infants, the device has an overall length of about 100 millimeters (mm), and a sleeve length of about 50 mm (i.e., the length of sleeve portion 34, 44). The stop surfaces 30, 40 have a width of about 19 mm and a depth of about 6 mm. The bowl has a length of about 9 mm, a width of about 5 mm, and a depth that varies along the length from about 1.5 mm near the stop surface to about 3.5 mm at the distal end. The upwardly inclined loop has a length of about 9 mm, a width of about 5 mm and a depth of about 2 mm. The opening 39 in the loop 38 has a generally tear-drop shape, with a length that is about 6 mm and a maximum width that is about 2 mm. Each of the stops have a teddy bear face design or shape that is about 16 mm in the length direction of the device, and sleeve portions 34, 44 connected to the head portions 32, 42 have generally circular cross sectional shapes with an outside diameter being about 10 mm. The shaft portion 16 of the light assembly 12 has a length of about 55 mm, and an outside diameter of about 8 mm. The battery compartment end portion 18 of the light assembly 12 has a generally circular shape with a diameter of about 25 mm. In other embodiments, the battery compartment end portion 18 may have other suitable shapes, such as oval, etc.

In one illustrative embodiment, the semi-translucent extraction elements 28, 38 and the semi-translucent sleeve portions 34, 44 are formed from polypropylene or another suitable polymeric material. The head portions 32, 42 of the extraction portions 26, 36 are formed from a soft rubber material, such as a thermoplastic elastomer (TPE) or a silicone rubber. In one illustrative embodiment, the housing sections 62, 64, the battery compartment cover 20, and the light power button 24 of the light assembly 12 are formed from high impact polystyrene or another suitable polymeric material. The carrying case 72 of the device 10 is formed from polypropylene or another suitable polymeric material. In one illustrative embodiment, the contact plates 46, 48 and the battery cover screw 22 are formed from stainless steel or another suitable metallic material. The materials used for the device 10 are free of any toxic or otherwise harmful or hazardous materials, such as phthalates or other plasticizers, that could be leached out during use. Also, the materials used for the housing of the device 10 are generally waterproof so as to allow for safe cleaning after every use.

Advantageously, because the device 10 described above includes a light emitting device 60, which is configured to illuminate at least a portion of a nostril or an ear canal, the device 10 is ideal for nighttime care when there is no natural light. The light emitting device 60 illuminates the nostril or the ear canal so that any blockages can be more easily visualized by the user and removed using the bowl 28 and/or loop 38.

Although the device 10 has been shown and described with respect to a certain embodiment or embodiments, it is apparent that aforedescribed device 10 can be embodied in many different forms and that many other modifications and variations are possible without departing from the spirit and scope of the claimed invention.

While exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A device for removing mucus from a nostril or earwax from an ear canal, comprising:
   a light assembly, the light assembly including a shaft portion extending outwardly from a base end portion, the light assembly further including a light emitting device, the light emitting device configured to emit light so as to illuminate at least a portion of a nostril or an ear canal; and
   an extraction portion configured to be coupled to the light assembly, the extraction portion including an extraction element and a stop located adjacent to the extraction element, the extraction element sized and configured to fit within the nostril or the ear canal for extracting mucus or earwax, and the stop sized to prevent insertion of the stop into the nostril or the ear canal and limit the depth that the extraction element is able to be inserted into the nostril or the ear canal;
   wherein the extraction portion is in a form of an extraction attachment that is configured to be removably coupled to the light assembly so that extraction attachments having different extraction elements are able to be interchangeably used with the light assembly, the extraction attachment comprising a head portion forming the stop and a sleeve extending from the head portion, the head portion being disposed between the extraction element and the sleeve of the extraction portion, the head portion extending outwardly beyond an outer wall of the sleeve so as to form the stop, the sleeve having a first end at the head portion and a second end oppositely disposed relative to the first end, the head portion forming a closed cap at the first end of the sleeve, the sleeve configured to be removably coupled to the shaft portion of the light assembly, the sleeve configured to fit over the shaft portion of the light assembly and extend to the base end portion of the light assembly, the second end of the sleeve being exteriorly disposed proximate to the base end portion of the light assembly, and the light emitting device of the light assembly being disposed inside the head portion when the extraction attachment is coupled to the light assembly.

2. The device according to claim 1, wherein the extraction element of the extraction portion is in a form of a bowl, the bowl including a sidewall and a bottom wall connected to the sidewall.

3. The device according to claim 2, wherein the bottom wall of the bowl is generally flat.

4. The device according to claim 2, wherein the bowl has a length and a width, the length of the bowl being from about 100% to about 300% of the width of the bowl.

5. The device according to claim 2, wherein the stop has a width that is at least 200% of the width of the bowl.

6. The device according to claim 1, wherein the extraction element of the extraction portion is in a form of a loop, the loop defining a loop opening.

7. The device according to claim 6, wherein the loop has a length and a width, the length of the loop being from about 100% to about 300% of the width of the loop.

8. The device according to claim 6, wherein the stop has a width that is at least 200% of the width of the loop.

9. The device according to claim 1, wherein the extraction element of the extraction portion is formed from a material that is at least semi-translucent so that the light emitted by the light emitting device is able to be transmitted through the extraction element.

10. The device according to claim 1, wherein the head portion of the extraction attachment is in a form of an animal head portion.

11. The device according to claim 1, wherein the light assembly further comprises a power source operatively coupled to the light emitting device, the power source configured to power the light emitting device, and the power source disposed inside a housing of the light assembly.

12. The device according to claim 11, wherein the light assembly further comprises a power switch operatively coupling the power source to the light emitting device, the power switch configured to activate and deactivate the light emitting device.

13. The device according to claim 1, wherein the light emitting device is in a form of a light-emitting diode.

14. A device for removing mucus from a nostril or earwax from an ear canal, comprising:
   a light assembly, the light assembly including a shaft portion extending outwardly from a base end portion, the light assembly further including a light emitting device, the light emitting device configured to emit light so as to illuminate at least a portion of a nostril or an ear canal;
   a first extraction portion configured to be coupled to the light assembly, the first extraction portion including a first extraction element and a first stop located adjacent to the first extraction element, the first extraction element sized and configured to fit within the nostril or the ear canal for extracting mucus or earwax, and the first stop sized to prevent insertion of the first stop into the nostril or the ear canal and limit the depth that the first extraction element is able to be inserted into the nostril or the ear canal; and
   a second extraction portion configured to be coupled to the light assembly, the second extraction portion including a second extraction element and a second stop located adjacent to the second extraction element, the second extraction element sized and configured to fit within the nostril or the ear canal for extracting mucus or earwax, and the second stop sized to prevent insertion of the second stop into the nostril or the ear canal and limit the depth that the second extraction element is able to be inserted into the nostril or the ear canal;

wherein the first extraction portion is in a form of a first extraction attachment that is configured to be removably coupled to the light assembly, and the second extraction portion is in a form of a second extraction attachment that is configured to be removably coupled to the light assembly, the first extraction portion and the second extraction portion configured to be interchangeably used with the light assembly; and wherein at least one of the first extraction attachment and the second extraction attachment comprises a head portion forming the first stop or the second stop and a sleeve extending from the head portion, the head portion being disposed between one of the first extraction element and the second extraction element and the sleeve, the head portion extending outwardly beyond an outer wall of the sleeve so as to form the first stop or the second stop, the sleeve having a first end at the head portion and a second end oppositely disposed relative to the first end, the head portion forming a closed cap at the first end of the sleeve, the sleeve configured to be removably coupled to the shaft portion of the light assembly, the sleeve configured to fit over the shaft portion of the light assembly and extend to the base end portion of the light assembly, the second end of the sleeve being exteriorly disposed proximate to the base end portion of the light assembly, and the light emitting device of the light assembly being disposed inside the head portion when the at least one of the first extraction attachment and the second extraction attachment is coupled to the light assembly.

15. The device according to claim 14, wherein the first extraction element of the first extraction portion is in a form of a bowl, the bowl including a sidewall and a bottom wall connected to the sidewall.

16. The device according to claim 14, wherein the second extraction element of the second extraction portion is in a form of a loop, the loop defining a loop opening.

17. The device according to claim 14, wherein the head portion of the at least one of the first extraction attachment and the second extraction attachment is in a form of an animal head portion.

18. The device according to claim 14, wherein at least one of the first extraction element and the second extraction element is formed from a material that is at least semi-translucent so that the light emitted by the light emitting device is able to be transmitted through the at least one of the first extraction element and the second extraction element.

* * * * *